United States Patent
Watanabe et al.

(10) Patent No.: US 7,829,853 B2
(45) Date of Patent: Nov. 9, 2010

(54) SAMPLE SURFACE OBSERVATION METHOD

(75) Inventors: Kenji Watanabe, Tokyo (JP); Masahiro Hatakeyama, Tokyo (JP); Yoshihiko Naito, Tokyo (JP); Kenji Terao, Tokyo (JP)

(73) Assignee: Ebara Corporation, Tokyo (JP)

( * ) Notice: Subject to any disclaimer, the term of this patent is extended or adjusted under 35 U.S.C. 154(b) by 247 days.

(21) Appl. No.: 12/244,139

(22) Filed: Oct. 2, 2008

(65) Prior Publication Data
US 2009/0090863 A1    Apr. 9, 2009

(30) Foreign Application Priority Data
Oct. 3, 2007    (JP) .............. 2007-259808

(51) Int. Cl.
G01N 23/00    (2006.01)
G01N 23/225    (2006.01)
H01J 37/26    (2006.01)

(52) U.S. Cl. .............. 250/307; 250/310; 250/492.22; 250/492.2; 250/492.3; 250/306

(58) Field of Classification Search .............. 250/307, 250/306, 310, 492.22, 492.2, 492.3
See application file for complete search history.

(56) References Cited

U.S. PATENT DOCUMENTS

2010/0032566 A1*    2/2010    Naito et al. .............. 250/307

2010/0133433 A1*    6/2010    Tanimoto et al. .............. 250/310

FOREIGN PATENT DOCUMENTS

| JP | 2004-193017 A | 7/2004 |
|----|---------------|--------|
| JP | 2005-235777 A | 9/2005 |
| JP | 2005-292157 A | 10/2005 |
| JP | 2007-080987 A | 3/2007 |

OTHER PUBLICATIONS

Japanese Office Action mail dated Sep. 29, 2009, issued in corresponding Japanese Application No. 2007-259808.

* cited by examiner

*Primary Examiner*—Nikita Wells
(74) *Attorney, Agent, or Firm*—Westerman, Hattori, Daniels & Adrian, LLP

(57)    ABSTRACT

A surface of a sample is observed by acquiring an image of the surface of the sample. An electron beam I irradiated onto the surface of the sample in which wiring including an insulation material and an electrically conductive material is formed. Electrons that acquired structure information regarding a structure of the surface of the sample are detected. An image of the surface of the sample is acquired by a result of the detection of electrons. The surface of the sample is observed using the acquired image of the surface of the sample. The electron beam is irradiated onto the surface of the sample in a state where a brightness of the insulation material and a brightness of the electrically conductive material in the image of the surface of the sample are set equal to each other.

10 Claims, 9 Drawing Sheets

NORMAL

MISSING DEFECT

OPEN DEFECT

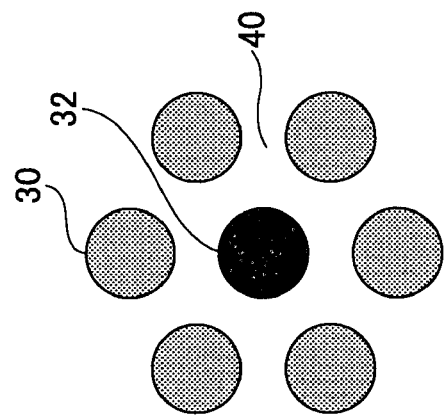
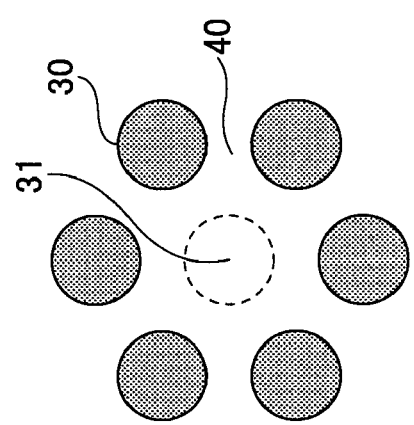
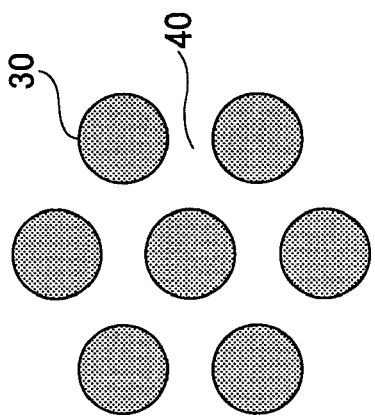
FIG.2A  NORMAL
FIG.2B  MISSING DEFECT (CENTER)
FIG.2C  OPEN DEFECT (CENTER)

FIG.10

| OPERATING CONDITION | NUMBER OF DETECTIONS | | DETECTION RATE [%] | |
|---|---|---|---|---|
| | MISSING | OPEN | MISSING | OPEN |
| 1 | 103(7) | 9(1) | 79.2 | 53.3 |
| 2 | — | 15(0) | — | 100 |
| 3 | 130(0) | — | 100 | — |

SAMPLE SURFACE OBSERVATION METHOD

BACKGROUND OF THE INVENTION

1. Field of the Invention

The present invention relates to a sample surface observation method and, more particularly, to a method of observing a surface of a sample having therein wiring containing an insulating material and an electrically conductive material.

2. Description of the Related Art

Conventionally, a sample surface observation method is known in which an electron beam is irradiated onto a surface of a sample such as a semiconductor wafer or the like so as to acquire a sample surface image by detecting electrons emitted from the sample surface, and detects a defect such as an open defect or a missing defect based on the acquired sample surface image (for example, refer to Patent Document 1).

FIGS. 1A, 1B and 1C are cross-sectional views of a part of a semiconductor wafer in which contact plugs are formed. FIG. 1A illustrates contact plugs 30, which are normal and grounded. In FIG. 1A, three contact plugs 30 are formed in an insulation layer 40. Each of the contact plugs 30 penetrates the insulation layer 40 so as to electrically connects layers above and under the insulation layer 40 to each other. Generally, the contact plugs 30 are formed by filling an electrically conductive material such as tungsten or copper into contact holes formed in the insulation layer 40.

FIG. 1B illustrates contact plugs including the contact plugs 30 and a contact plug 31 of a missing defect. In FIG. 1B, the contact plug 31 in the middle among the contact plugs 30 to be formed originally is not formed and in a state where the contact plug 32 is missed. As such, the missing defect refers to a defect that a contact hole is not formed at a position where it must be formed during, for example, an exposure process or etching process. The missing defect may cause a problem in that layers above and under the contact plug 31 are not electrically connected to each other.

FIG. 1C illustrates contact plugs including the contact plugs 30 and a contact plug 32 of an open defect. In FIG. 1C, the contact plug 32 in the middle among the contact plugs 30 is formed in an incomplete state where an electrically conductive material such as tungsten or copper is filled insufficiently so that the plug does not penetrate the insulation layer 40, and layers above and under the insulation layer 40 are not electrically connected to each other. As such, the open defect refers to a defect that an electrically conductive material such as tungsten or copper is not appropriately filled in a contact hole. The open defect may cause a problem in that the layers above and under the contact plug 32 are not electrically connected to each other or a resistance between the layers above and under the contact plug 32 increases greatly.

According to a conventional sample surface observation method, the missing defect and the open defect illustrated in FIGS. 1B and 1C are detected by acquiring a wafer surface image acquired from a surface of a semiconductor wafer and comparing a position where a contact plug is to be formed with a position corresponding to the normal contact plug 30 to obtain a difference in image brightness (intensity) in the wafer surface image.

FIGS. 2A, 2B and 2C are illustrations of wafer surface images acquired by a conventional sample surface observation method. FIG. 2A illustrates a wafer surface image in which the normally grounded contact plugs 30 are formed as illustrated in FIG. 1A. In FIG. 2A, the normally grounded contact plugs are displayed in the same brightness.

FIG. 2B illustrates a wafer surface image in which the contact plugs 30 and the contact plug 31 of the missing defect illustrated in FIG. 1B are formed. In FIG. 2A, the contact plug 31 of the missing defect at the center is displayed in the same brightness as the surrounding insulation layer 40.

FIG. 2C illustrates a wafer surface image in which the contact plugs 30 and the contact pug 32 of the open defect illustrated in FIG. 1C are formed. In FIG. 2C, a part of the contact plug 32 of the open defect at the center is displayed in a higher brightness than the part of the normal contact plugs 30 because there is a difference in brightness between the defective contact plug 32 and the normal contact plugs 30.

Thus, in the conventional sample surface observation method, the detection and classification of the missing defect and the open defect is carried out based on a difference in a gradation level such as a monochrome image brightness difference in the wafer surface image.

It should be noted that, as a method of detecting a pattern, which is not electrically connected to other parts, formed in a semiconductor device wafer, there is known a testing method of a semiconductor device which can detects an electric abnormality quickly by detecting a change in an amount of secondary electrons due to a potential difference in a pad (for example, refer to Patent Document 2). According to this method, a conductive pattern extending in a row direction and a column direction and a wiring patter having a predetermined conductive part connected to the pattern are provided in a TEG (Test Element Group) area of a semiconductor device. A change in an amount of secondary electrons is detected by scanning the conductive part by an electron beam.

Patent Document 1: Japanese Laid-Open Patent Application No. 2005-235777

Patent Document 2: Japanese Laid-Open Patent Application No. 2007-80987

However, according to the structure recited in the above-mentioned Patent Document 1, there is a problem in that the detection of a missing defect and an open defect may be difficult because a gradient difference of each position is too small (whose difference depending on a material of the contact plug 30 or a kind of the insulation layer 40). Additionally, especially for the open defect, there is a problem in that it is extremely difficult to detect a defect and classify a kind of the defect because there are a case where the portion of the contact plug 32 having an open defect has a brightness higher than the portion of the normal contact plug 30 (changes into darker black) and a case where the part of the contact plug 32 has a brightness lower than the portion of the normal contact plug 32 (changes into brighter white).

That is, in the conventional sample surface observation method, there is a problem in that it is difficult to discriminate any defects from the normal contact plug 30, which makes the defect detection difficult because the detections of the missing defect and the open defect are performed simultaneously in the same condition.

According to the structure recited in the above-mentioned Patent Document 2, it is possible to perform a general test in a manufacturing condition of a semiconductor device by using TEG. However, a specific and individual test of a pattern actually formed in a semiconductor device must be carried out according to a different method, and there is a problem in that the method of the Patent Document 2 is not applicable to testing an entire surface of a semiconductor device.

SUMMARY OF INVENTION

It is a general object of the present invention to provide an improved and useful sample surface observation method in which the above-mentioned problems are eliminated.

A more specific object of the present invention is to provide a sample surface observation method which can easily detect a defect in detecting a defect of a wiring structure by acquiring a sample surface image in which a difference in brightness between a defective position and a normal position is large.

In order to achieve the above-mentioned objects, there is provided according to one aspect of the present invention a sample surface observation method of observing a surface of a sample by acquiring an image of the surface of the sample, the sample surface observation method comprising: irradiating an electron beam onto the surface of the sample in which a pattern including an insulation material and an electrically conductive material is formed; detecting electrons that acquired structure information regarding a structure of the surface of the sample; acquiring an image of the surface of the sample by a result of the detection of electrons; and observing the surface of the sample using the acquired image of the surface of the sample, wherein the electron beam is irradiated onto the surface of the sample in a state where a brightness of the insulation material and a brightness of the electrically conductive material in the image of the surface of the sample are set equal to each other.

The above-mentioned sample surface observation method may further comprise detecting, as an open defect in the surface of the sample, a brightness of a part different from a brightness of the insulation material and a brightness of the electrically conductive material in the image of the surface of the sample. Thus, an open defect can be picked up as a brighter part than other areas such as an insulator or a conductive area.

Additionally, there is provided according to another aspect of the present invention a sample surface observation method of observing a surface of a sample by acquiring an image of the surface of the sample, the sample surface observation method comprising: irradiating an electron beam onto the surface of the sample in which wiring including an insulation material and an electrically conductive material is formed; detecting electrons that acquired structure information regarding a structure of the surface of the sample; acquiring an image of the surface of the sample by a result of the detection of electrons; and observing the surface of the sample using the acquired image of the surface of the sample, wherein the electron beam is irradiated onto the surface of the sample in a state where a difference in brightness between said insulation material and said electrically conductive material in the image of the surface of the sample is maximum. Thus, a sample surface image in which a missing defect can be detected easily is acquired.

In the above-mentioned sample surface observation method, the state where a difference in brightness between the insulation material and the electrically conductive material in the image of the surface of the sample is maximum is determined in a mirror electron area where electrons that has acquired the structure information of the surface of the sample turn into mirror electrons. Thus, a sample surface image in which a missing defect can be detected easily is acquired.

Additionally, in the above-mentioned sample surface observation methods, a setting of a state based on the brightness of said insulation material and the brightness of said electrically conductive material in the image of the surface of the sample may be performed by adjusting a landing energy when irradiating the electron beam onto the surface of the sample. The electron beam may be a surface beam that irradiates a predetermined two-dimensional area. The electron beam may be irradiated onto the surface of the sample while gradually increasing a landing energy for a plurality of times.

Other objects, features and advantages of the present invention will become more apparent from the following detailed description when read in conjunction with the accompanying drawings.

BRIEF DESCRIPTION OF DRAWINGS

FIG. 2A illustrates a wafer surface image in which normally grounded contact plugs are formed as illustrated in FIG. 1A;

FIG. 2B illustrates a wafer surface image in which contact plugs including a contact plug of a missing defect illustrated in FIG. 1B are formed;

FIG. 2C illustrates a wafer surface image in which contact plugs including a contact plug of an open defect illustrated in FIG. 1C are formed;

FIG. 10 is an illustration showing a result of a defect detection using a sample surface observation method according to the embodiment of the present invention.

DETAILED DESCRIPTION OF THE PREFERRED EMBODIMENT

A description will now be given, with reference to the drawings, of an embodiment of the present invention.

Figure 1A:
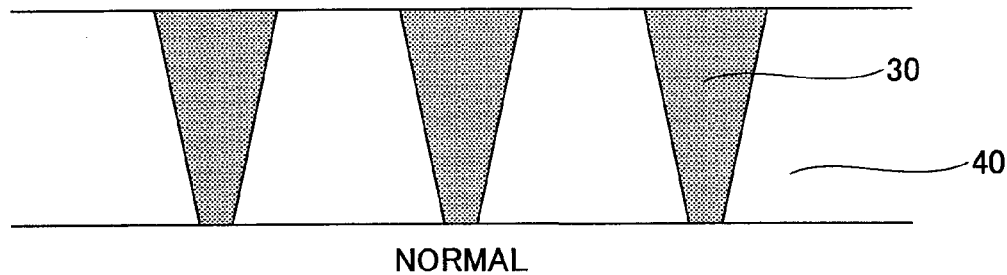
FIG. 1A illustrates contact plugs, which are normal and grounded.
Figure 1B:
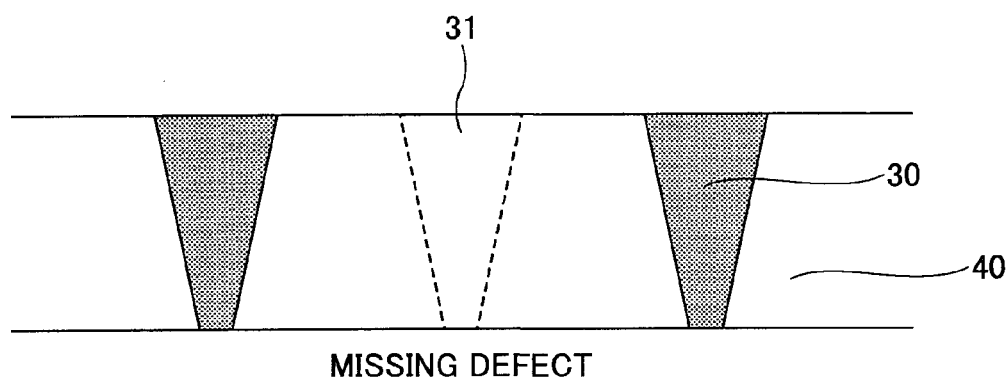
FIG. 1B illustrates contact plugs including normal contact plugs and a contact plug of a missing defect.
Figure 1C:
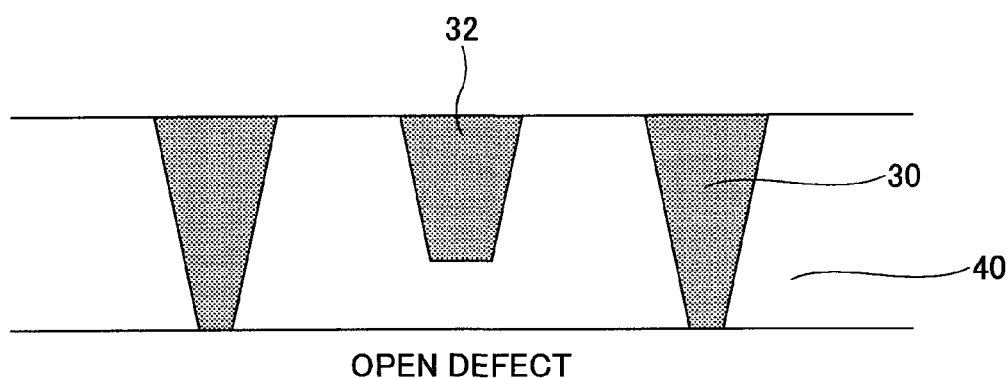
FIG. 1C illustrates contact plugs including normal contact plugs and a contact plug of an open defect.
Figure 3:
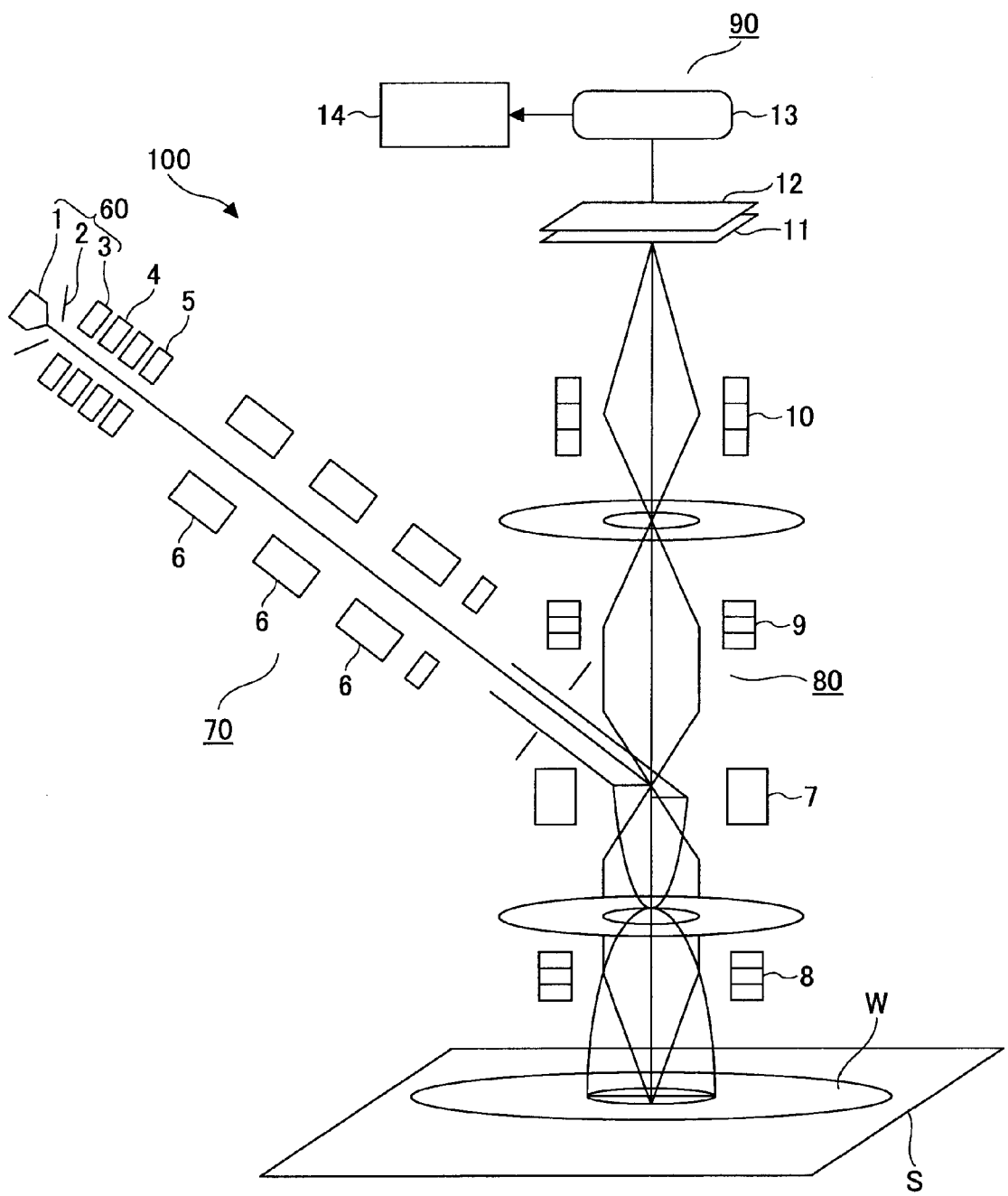
FIG. 3 is an illustration of an electron beam apparatus performing a sample surface observation method according to an embodiment of the present invention.

FIG. 3 is an illustration of an electron beam apparatus 100, which performs a test surface observation method according to an embodiment of the present invention. In FIG. 3, the electron beam apparatus 100 is equipped with an electron beam projection part 60, a primary electron optical system 70, a secondary electron optical system 80 and an electronic detection part 90.

The electronic beam projection part 60 is means for generating and projecting an electron beam. The electron beam projection part 60 is equipped with an electron gun 1, a Wehnelt electrode 2 and an anode 3. An electron beam emitted from a cathode electrode (not shown in the figure) of the electron gun 1 is controlled in its amount of emitted electrons by the Wehnelt electrode 2, and is accelerated by the anode 3 and enters the primary electron optical system 70.

The primary electron optical system 70 is means for guiding the electron beam projected from the electron beam projection part 60 to be irradiated onto a surface of a sample W. The primary electron optical system 70 is equipped with an electrostatic lens 4, an opening 5, a plurality of stages of quadrupole lenses 6, an E×B separator 7 and an object lens 8. The primary electron optical system 70 adjusts and shapes the electron beam projected from the electron beam projection part 60 by using the electrostatic lens 4, the opening 5 and the quadrupole lenses 6. Then the primary electron optical system 70 changes a traveling direction of the electron beam by using the E×B separator 7 so that the primary electron beam is incident perpendicularly to the surface of the sample W placed on a stage S, and forms the electron beam into a desired cross section by the object lens 8 and irradiates the electron beam onto the surface of the sample W.

The sample W can be any materials if they contain an insulation material and an electrically conductive material in a sample surface thereof. The sample surface observation method according to the present embodiment is suitable for observing a semiconductor device formed in a semiconductor wafer.

The stage S may be configured and arranged to be movable in two orthogonal directions X and Y in a horizontal plane and rotatable, if necessary, in the X-Y plane. According to the moving functions, the surface of the sample W can be scanned by the electron beam.

Although not illustrated, means for adjusting a potential of the sample surface may be provided in the vicinity of the stage S. By adjusting a cathode voltage of the electron gun 1 and the potential of the sample surface, a landing energy when irradiating the electron beam onto the surface of the sample W can be adjusted and controlled. As explained in detail later, in the sample surface observation method according to the present embodiment, a material contrast of the sample W is adjusted by adjusting the landing energy when irradiating the electron beam onto the sample W. Accordingly, the electron beam apparatus 100 may be equipped with sample potential adjusting means as means for adjusting such a landing energy.

It should be noted that the electron beam is irradiated onto the sample surface by operations of the electron beam projection part 60 and the primary electron optical system 70 so that an electron beam irradiation process is performed.

The secondary electron optical system 80 is means for guiding electrons, which have acquired structure information of the sample surface by the electron beam irradiation process, to the electron detection part 90. The secondary electron optical system 80 is equipped with the object lens 8, the E×B separator 7, a first stage condensing lens 9 and a second stage condensing lens 10. By irradiating the electron beam, mirror electrons, which have acquired the structure information of the sample surface, and secondary electrons including reflection electrons and rear scattering electrons pass through the secondary electron optical system 80, and is guided to the electron detection part 90.

The mirror electrons are electrons of the electron beam irradiated toward the sample W in the electron beam irradiation process and reflected without colliding with the sample surface. The secondary electron containing the reflection electrons and the rear scattering electrons are electrons emitted from the sample surface by the electronic beam being irradiated onto the sample W in the electron beam irradiating process. Because any electrons have acquired structure information of a two-dimensional or three-dimensional structure of the sample surface, they can be used to acquire the structure information of the sample surface.

The electron detection part 90 is means for detecting the electrons, which have acquired the structure information of the sample surface, and acquiring a sample surface image. The electron detection part 90 is equipped with a MCP (Micro-Channel Plate) 11, a fluorescence board 12, a TDI-CCD (Time Delay Integration-Charge Coupled Device) detector 13 and an image processing part 14. The MCP 11 is electron intensifying means for intensifying incident electrons. The fluorescence board 12 changes electrons supplied from the MCP 11 into an optical signal. The TDI-CCD detector 13 receives the optical signal from the fluorescence board 12, changes the received optical signal into an electric signal according to an intensity of the optical signal, and outputs the electric signal to the image processing part 14. Here, since the light which the TDI-CCD detector 13 receives from the fluorescence board 12 is a light based on the electrons which have acquired the structure information of the sample surface, an amount of light varies according to the structure of the sample surface. Accordingly, the electric signal which the TDI-CCD detector 13 outputs is an electric signal having a voltage varying according to the structure of the sample surface. The image processing part 14 carries out an A/D conversion on the received electric signal, and forms a digital image. Such an operation is carried out through the scanning period of the sample surface, and consequently the image processing part 14 can output the image of the surface of the sample.

It should be noted that according to the operations of the secondary electron optical system 80 and the electron detection part 90, the electrons which have acquired the structure information of the sample surface are detected and the sample surface image acquiring process is performed to acquire the sample surface image.

Although the sample surface observation method according to the present embodiment can be performed using the above-mentioned electronic beam apparatus 100, the electronic beam equipment 100 shown in FIG. 3 is merely an example, and various types of electron beam apparatus may be applicable. If the electron beam irradiating process to irradiate an electron beam onto a sample surface and a sample image acquiring process to acquire an image of a sample based on electrons which have acquired the structure information of the sample surface can be performed, the sample surface observation method according to the present embodiment can be applied to various forms of the electron beam apparatus 100.

A description will now be given, with reference to FIGS. 4 through 8, of the sample surface observation method according to the present embodiment.

Figure 4:
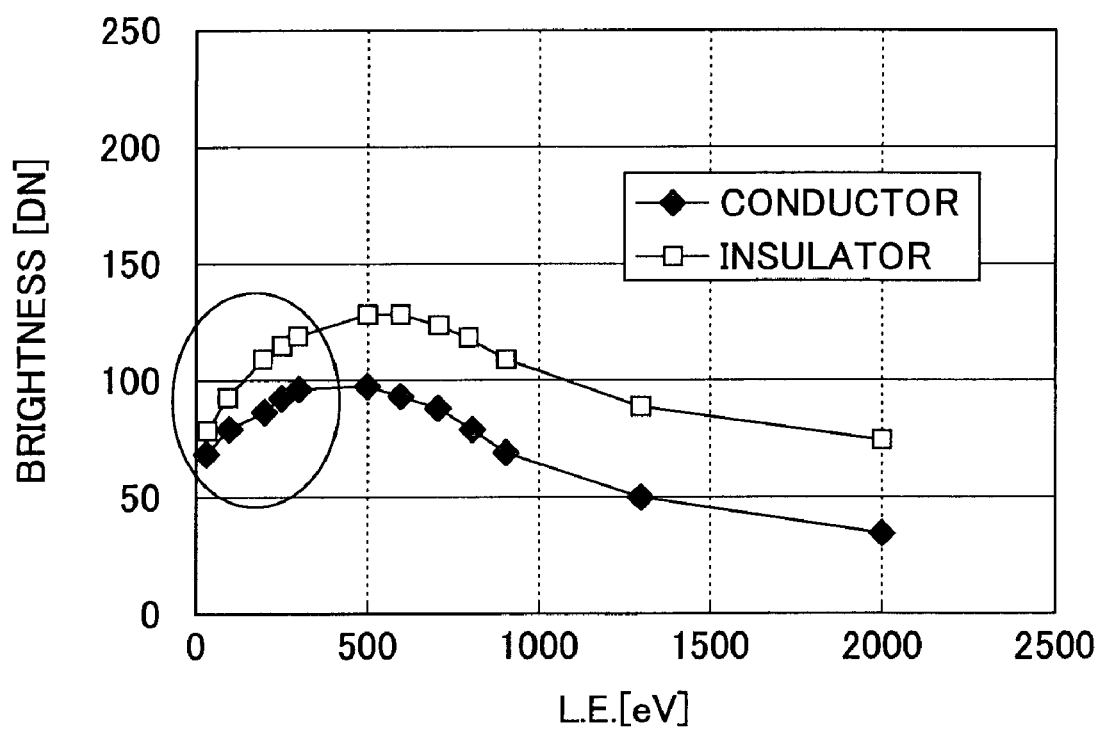
FIG. 4 is a graph showing a gradient difference between an electrically conductive material and an insulation material according to a landing energy.

FIG. 4 is a graph showing image brightness of an electrically conductive material and an insulation material according to a landing energy of an electron beam. The graph of FIG. 4 is obtained by varying a landing energy of the electron beam incident on a sample surface when acquiring an image of the sample by irradiating the electron beam onto the sample surface and measuring the image brightness of the insulation material and the electrically conductive material in the sample surface image acquired at that time. In FIG. 4, the horizontal axis represents a landing energy L (eV) when the electron beam is irradiated onto the sample surface, and the vertical axis represents a brightness (DN).

The landing energy refers to a landing acceleration voltage when the electron beam is incident on the sample surface, and can be expressed by a potential difference between the cathode potential of the electron gun 1 and the potential of the sample surface (a retarding voltage). Accordingly, for example, in the case of the electron beam apparatus 100 shown in FIG. 3, the landing energy can be adjusted by controlling the cathode voltage of the electron gun 1 and/or sample voltage adjusting means (not shown in the figure).

The brightness of the electrically conductive material and the insulation material with respect to the landing energies are shown in FIG. 4. A brightness of the insulation material is higher than that of the electrically conductive material in an area where the landing energy is equal to or larger than 100 (eV).

Figure 5:
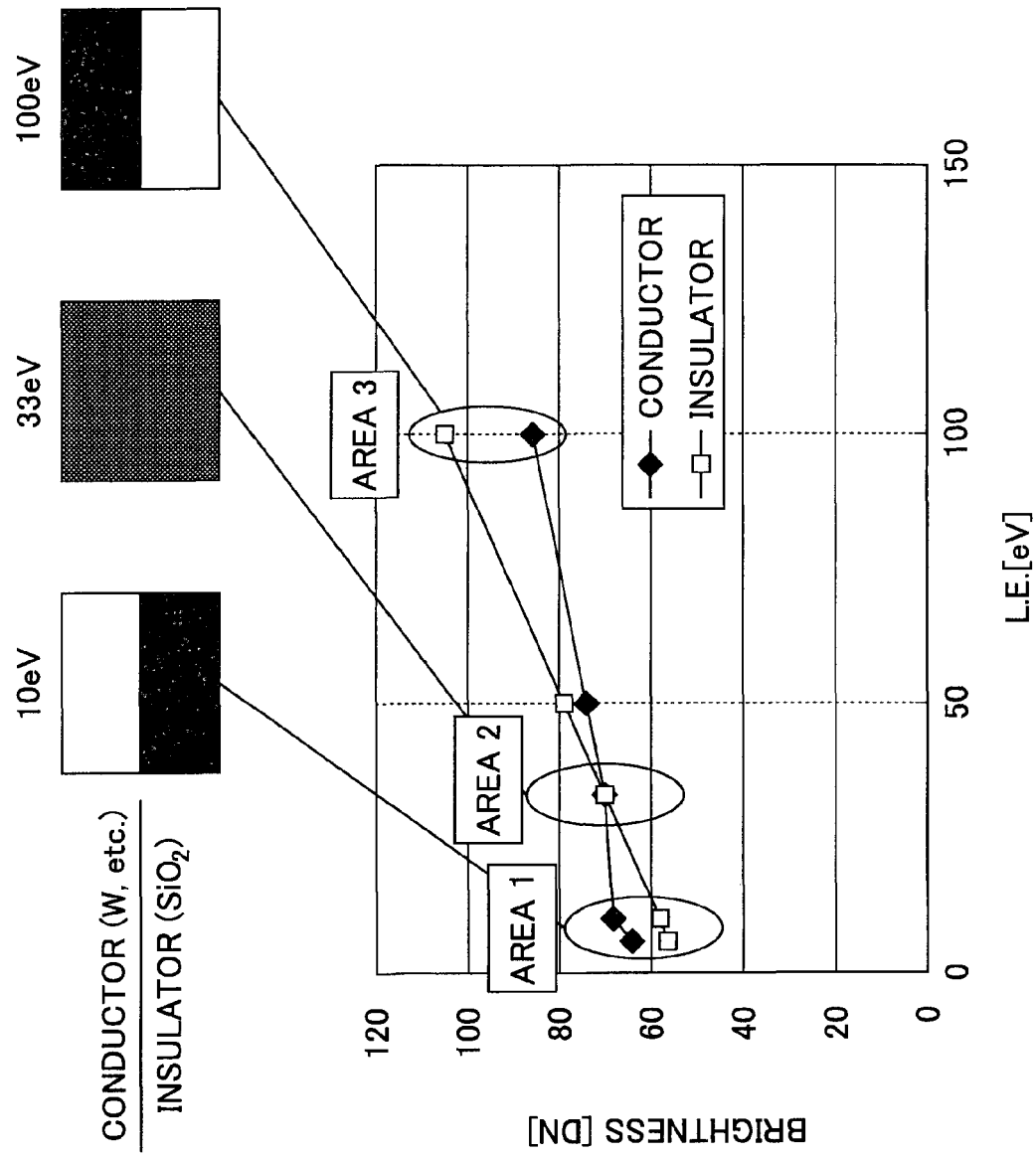
FIG. 5 is a graph showing a brightness change in an area where a landing energy is equal to or smaller than 100 eV.

FIG. 5 is an enlarged graph of a part encircled by a circle in FIG. 4, and shows a difference in brightness between the electrically conductive material and the insulation material corresponding to the landing energies of the electron beam similar to FIG. 4. In FIG. 5, brightness changes according to a change in the landing energy in an area where the landing energy is equal to or smaller than 100 (eV) is indicated.

In FIG. 5, it can be appreciated that the area where the landing energy is equal to or smaller than 100 (eV) includes an area 1, an area 2 and an area 3. In the area 1, the brightness of the electrically conductive material is higher than the insulation material. In the area 2, the electrically conductive material and the insulation material exhibit almost the same brightness. In the area 3, the insulation material exhibits a higher brightness than the electrically conductive material.

As shown in an upper part of the graph of FIG. 5, because, for example, the landing energy 10 (eV) corresponds to the area 1 and the brightness of the electrically conductive material is higher than the brightness of the insulation material in the area 1, an image of the sample is acquired, in which the electrically conductive material is displayed in white and the insulation material is displayed in black.

Similarly, because, for example, a point of the landing energy 33 (eV) corresponds to the area 2 and brightnesses of the electrically conductive material and the insulation material are equal to each other in the area 2, an image of the sample is acquired, in which the brightnesses of both the electrically conductive material and the insulation material are equal to each other, that is, both the electrically conductive material and the insulation material are displayed in gray.

Because, for example, the landing energy 100 (eV) corresponds to the area 3 and the brightness of the electrically conductive material is higher than the brightness of the insulation material in the area 3, an image of the sample is acquired, in which the insulation material is displayed in white and the electrically conductive material is displayed in black.

Thus, the gradation levels of the electrically conductive material and the insulation material in the acquired image of the sample can be selected by changing the landing energy of the electron beam. That is, for example, if it is desired to equalize the gradation levels of the electrically conductive material and the insulated material so as to set a material contrast to zero, what is necessary if to selectively set the landing energy value contained in the area 2, which results in acquisition of an image of the sample in which the gradation level of a wiring material other than the electrically conductive material and the insulation material is different.

On the other hand, if it is desired to increase the difference between the gradation levels of the electrically conductive material and the insulation material in the image of the sample to make the material contrast higher, what is necessary is to select a point at which the difference between the electrically conductive material and the insulation material is larger from among the area 1 and area 3. Further, if it is desired to set the brightness of the electrically conductive material lower than the brightness of the insulation material, what is necessary is to selectively set a landing energy value contained in the area 1. On the other hand, if it is desired to set the brightness of the electrically conductive material higher than the brightness of the insulation material, what is necessary is to selectively set a landing energy value contained in the area 3.

Thus, by using a relationship between brightness values of an electrically conductive material and an insulation material according to the landing energy, a gradation level adjustment according to materials in an acquired image of a sample can be achieved, thereby enabling an acquisition of an image of the sample corresponding to a defect as a target to be detected.

A description will now be given of the sample surface observation method for detecting an open defect and a missing defect, with reference to the graph of FIG. 5, which indicates a difference between brightness values corresponding to a landing energy.

Figure 6A:
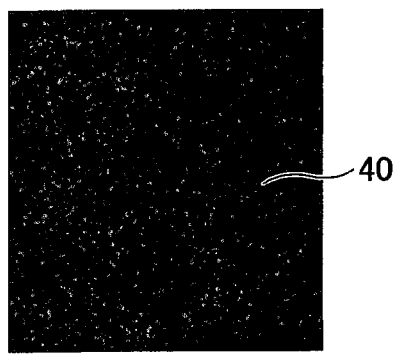
FIG. 6A is an illustration of a surface image of a sample in which a normal contact plug is formed.
Figure 6B:
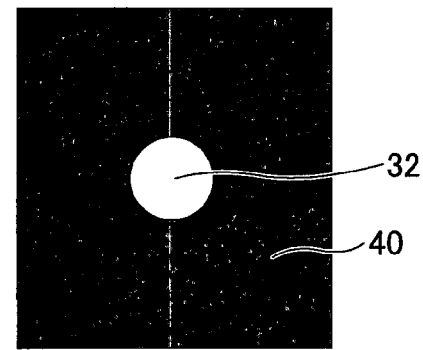
FIG. 6B is an illustration of a surface image of a sample in which a contact plug of an open defect is formed.

FIGS. 6A and 6B are illustrations of images of a sample which is acquired when observing the sample surface at a landing energy of the area 2 shown in FIG. 5. FIG. 6A illustrates an image of the surface of the sample in which the normal contact plugs 30 are formed. In FIG. 6A, because the sample surface is observed in an area of a landing energy, which makes a difference in brightness between the insulation material and the electrically conductive material is zero, the surface layer of the sample W in which the normal contact plugs 30 are formed is constituted by only the insulation material and the electrically conductive material. Thus, the image of the sample has uniform brightness, that is, a unicolor image is acquired as shown in FIG. 6A.

The landing energy at which the brightness values of the electrically conductive material and the insulation material are equalized in the area 2 of FIG. 5 is about 33 (ev), which is in a low energy area. In such a low energy area, when the electron beam is irradiated onto the sample surface, the inventors have confirmed that a probability of mirror electrons being reflected by a surface of a sample is high. Thus, although mirror electrons are mainly and effectively used to observe a surface of a sample in the sample surface observation method according to the present embodiment, there may be a case where secondary electrons or reflection electrons are emitted from a surface of a sample, and, thus, the electron detector 40 detects secondary electrons or reflection electrons without discrimination to use those electrons in acquiring a surface image of a sample.

FIG. 6B illustrates an image of a surface of a sample in which a contact plug of an open defect is formed. In FIG. 6B, a brightness at a center portion in the sample surface image is high, that is, a brightness at the center portion is high. Accordingly, the center portion clearly appears in white and distinguishable from the surrounding area. The white portion corresponds to the contact plug 32 having an open defect. Thus, the contact plug 32 of an open defect can be clearly detected by equalizing the brightness of the insulation material and the brightness of the electrically conductive material to each other.

Although the contact plug 32 of an open defect also consists of an insulation material and an electrically conductive material as far as a material is concerned, a difference in brightness between the insulation material and the electrically conductive material is set to zero in consideration of a case where the insulation layer 40 is filled in a thickness direction by each of the insulation material and the electrically conductive material. Thus, in the state where the insulation material and the electrically conductive material are mixed such as in the contact plug 32 of an open defect, a resistance value thereof is different from that of the insulation material and the electrically conductive material. Thereby, an image of a surface of a sample, in which the contact plug 32 of an open defect is visually emphasized such as shown in FIG. 6B, can be acquired. Additionally, a position observed using an electron beam is an area of a surface layer close to the surface of the sample W, and the adjustment of the state of brightness of the insulation material and the electrically conductive material is performed on the surface layer of the sample. Thus, the open defect, which is a defect in a direction of thickness in a surface of a sample, can also be detected clearly. Further, since the above-mentioned mirror electrons and the reflection electrons or the secondary electrons are detected in an overlapped state, the thickness (dark and bright) is more emphasized than a conventional one, thereby enabling an acquisition of an image of a higher contrast.

As mentioned above, in the sample surface observation method according to the present embodiment, a landing energy is set so that the insulation material and the electrically conductive material have the same brightness in the sample surface image and the electron beam is irradiated onto the surface of the sample to acquire the image of the sample surface, and, thereby, the contact plug 32 of an open defect formed in the surface layer of the sample W can be surely detected.

Figure 7A:
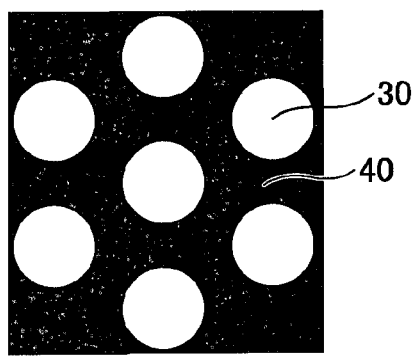
FIG. 7A is an illustration of a surface image of a sample in which normal contact plugs are formed.
Figure 7B:
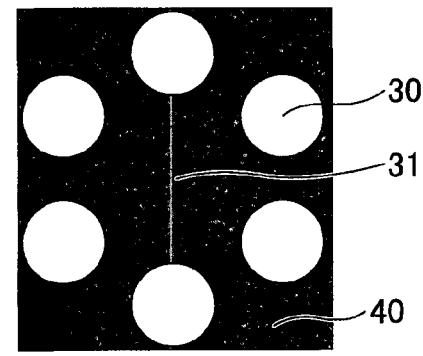
FIG. 7B is an illustration of a surface image of a sample which includes a missing defect of a contact plug.

FIGS. 7A and 7B are illustrations of images of surfaces of samples observed with a landing energy of the area 1 of FIG. 5. FIG. 7A illustrates an image of a surface of a sample in which the normal contact plugs 30 are formed. Because the electrically conductive material has a higher brightness than the insulation material in the area 1 of FIG. 5, the normal contract plugs 30, which are filled by the electrically conductive material such as tungsten or copper, have a high brightness in FIG. 7A and the surrounding area of the insulation layer 40 has a low brightness. That is, the brightness of the positions corresponding to the contact plugs 30 is low (black), and the brightness of the position corresponding to the insulation layer 40 is high (white). Because a difference in brightness between the conductive material and the insulation material is large in the state of the landing energy in the area 1, an image of a surface of a sample can be acquired, in which the normal contact plugs 30 can be clearly distinguishable from the surrounding insulation layer 40 by a large difference in brightness.

FIG. 7B illustrates an image of a surface of a sample containing the contact plug 31 of a missing defect. In FIG. 7B, the contact plug 31 supposed to be formed at the center of the image is not formed actually, which generates a missing defect. In the case of the missing defect, the contact plug 31 is not formed at all, and a position corresponding to the missing defect is filled by the insulation material and is displayed by the same gradation level (brightness) as the surrounding insulation layer 40. Thus, the position of the missing defect can be specified by comparing the sample surface image with the image of the normal contact plugs 30.

If, for example, the normal contact plugs 30 are regularly arranged at a fixed interval, a distance between the adjacent normal contact plugs 30 is calculated so that the missing defect of the contact plug 31 is detected by referring to the distance.

If the contact plugs 30 are arranged irregularly, a reference image of a surface of a sample including a certain area in which the normal contact plugs 30 are formed is acquired. Then, an image of a surface of a sample corresponding to the same area is acquired and compared with the reference image so as to perform pattern matching, thereby detecting the contact plug 31 of a missing defect based on matching of the images.

As mentioned above, the comparison of the sample surface images for detecting the contact plug 31 of a missing defect may be performed at a position where the contact plug is supposed to be formed or may be performed with sample surface images containing a surrounding area. In any detection of a missing defect, the electron beam is irradiated onto the surface of the sample in a state where the difference in brightness between the normal contact plug 30 and the contact plug 31 of a missing defect is maximum so as to acquire the image of the surface of the sample. Thus, an image of a surface of the sample, in which the difference in brightness between the contact plug 30 and contact plug 31 of a missing defect is large, and, thereby, the detection of a missing defect can be easily and surely performed.

Figure 8A:
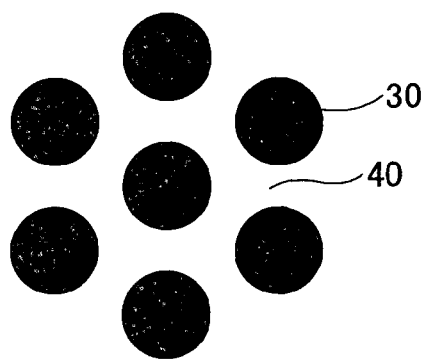
FIG. 8A is an illustration of a surface image of a sample in which normal contact plugs are formed.
Figure 8B:
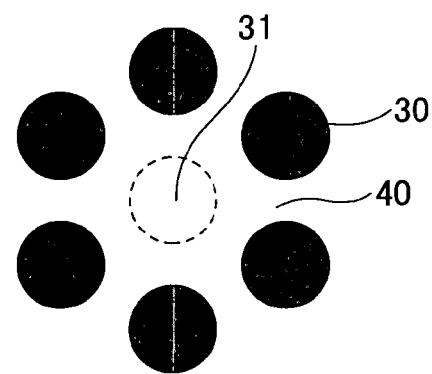
FIG. 8B is an illustration of a surface image of a sample which includes a missing defect of a contact plug.

FIGS. 8A and 8B are illustrations of images of surfaces of samples observed with a landing energy of the area 3 of FIG. 5. In the state of the area 3, the brightness of the insulation material is higher than the brightness of the electrically conductive material and the difference in brightness therebetween is maximum.

FIG. 8A illustrates an image of a surface of a sample in which the normal contact plugs 30 are formed. In FIG. 8A, the positions of the normal contract plugs 30, which are filled by the electrically conductive material such as tungsten or copper, have a low brightness, and an image having a high brightness is formed. On the other hand, the surrounding area of the insulation layer 40 formed of the insulation material has a high brightness, and the corresponding image has a high brightness and is displayed in white. Because a difference in brightness between the conductive material and the insulation material is maximum, an image of a surface of a sample can be acquired, in which the normal contact plugs 30 in black is clearly distinguishable from the insulation layer 40 displayed in white.

On the other hand, FIG. 8B illustrates an image of a surface of a sample containing the contact plug 31 of a missing defect. In FIG. 8B, the portion of the contact plug 31 supposed to be formed at the center of the image is formed of the insulation material, the portion of the missing contact plug 31 is displayed by the same gradation level as the surrounding insulation layer 40. It should be noted that although the portion of the contact plug 31 of a missing defect is indicated virtually for the sake of easy understanding, it is displayed actually as an image having no boundary between the surrounding insulation layer 40.

Also in the thus-acquired image of the sample surface, a missing defect can be detected by the same method as that explained with reference to FIG. 7B. That is, if the normal contact plugs 30 are regularly arranged at a fixed interval, a missing defect can be detected by comparing the image at the position of the missing defect with the image of the surrounding normal contact plugs 30. On the other hand, even if the contact plugs 30 are arranged irregularly, the missing defect can be detected by comparing the images of the surface of the sample with each other and performing pattern matching.

When detecting a missing defect in the state of the area 3 shown in FIG. 8A, since the difference in brightness between the normal contact plugs 30 formed by the electrically conductive material and the contact plug 31 of a missing defect formed by the insulation material is in a maximum state, the difference in gradation level between both is large, and a missing defect can be detected clearly and surely.

It should be noted that, when detecting a missing defect, whether to perform the sample surface observation in the state where the brightness of the electrically conductive material is higher than the brightness of the insulation material in the area 1 of FIG. 5 or in the state where the brightness of the insulation material is higher than the brightness of the electrically conductive material in the area 3 is appropriately selected according to an application. In any mode, because the difference in brightness between the electrically conductive material and the insulation material in the image of the surface of the sample is in the maximum state, the detection of a missing defect as a target to be can be easily and surely performed.

A description will now be given of a result of the detection by the sample surface observation method according to the present embodiment.

Figure 9:
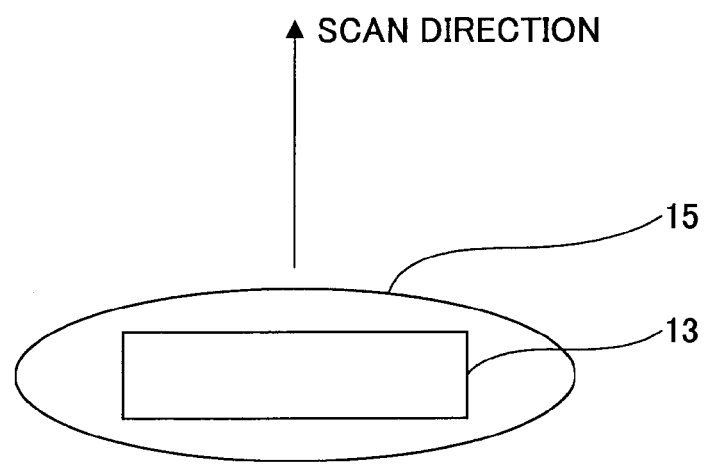
FIG. 9 is an illustration indicating a positional relationship between a picture taking area of a TDI-CCD sensor and an electron beam on a sample surface.

FIG. 9 is an illustration showing a positional relationship between the image taking area (viewing area) of the TDI-CCD sensor 13 and the electron beam 15. By using the electron beam 15 having a two-dimensional area, observation of a surface of a sample was performed in a condition where the acceleration voltage was −4033 (eV), the voltage of the surface of the sample was −4000 (eV) and the landing energy was 33 (eV). The acceleration voltage refers to the voltage of the cathode of the electron gun 1. The landing energy was adjusted by increasing and decreasing the voltage of the cathode or the voltage (retarding voltage) of the surface of the sample. Because this condition is the same as the condition indicated by the area 2 of FIG. 5, the electron beam 15 was irradiated onto the surface of the sample in the state where the brightness of the electrically conductive material and the brightness of the insulation material are equal to each other in the image of the surface of the sample so as to acquire the image of the surface of the sample. Thus, when there is the contact plug 32 of an open defect, it was displayed by a gradation level different from the surrounding area, and an image in which the contact plug 32 is emphasized was acquired and an open defect was detected.

On the other hand, when detecting a missing defect, the electron beams 15 shown in FIG. 9 was used, and the acceleration voltage was set to −4010 (eV), the voltage of the surface of the sample was set to −4000 (eV) and the landing energy was set to 10 (eV). The electron beam 15 was irradiated onto the surface of the sample in the same condition as the area 1 of FIG. 5. In this case, as explained with reference to FIGS. 7A and 7B, the positions of the contact plugs 30 popped up in white from the surrounding insulation layer 40, and the positions of the contact plug 31 of a missing defect was displayed in black as the same as the surrounding area. Based on the thus-acquired image of the sample, an image comparison was performed for detecting a missing defect, and the missing defect was detected.

FIG. 10 is an illustration of a result of the defect detection by the sample surface observing method according to the present embodiment. In FIG. 10, an operating condition 1 indicates a result of detection of a missing defect and an open defect by a conventional sample surface observing method. An operating condition 1 indicates a result of detection of an open defect by the condition of the area 2 according to the present embodiment. An operating condition 3 indicates a result of detection of a missing defect by the condition of the area 1 according to the present embodiment. It should be noted that, in FIG. 10, "MISSING" indicates a missing defect, and "OPEN" indicates an open defect. Additionally, a number in parentheses indicates a number of false defects.

In FIG. 10, in the operating condition according to a conventional sample surface observation method, the detection rate of a missing defect is 79.2%, and the detection rate of an open defect is 53.3%. On the other hand, in the operating condition 2 according to the sample surface observation method according to the present embodiment, no missing defect is detected but 100% of an open defect is detected. Similarly, in the operating condition 3 according to the sample surface observation method according to the present embodiment, no open defect is detected but 100% of a missing defect is detected. It can be appreciate that the detection rate is improved as compared to the conventional method, and also no false defect is detected.

Thus, by changing the condition of irradiating the electron beam 15 according to a kind of defect as a target to be detected, and by irradiating the electron beam 15 onto a surface of a sample in a state appropriate for detecting an open defect and a missing defect, a defect as a target to be detected can be surely detected.

It should be noted that the state where the brightness of the insulation material and the brightness of the electrically conductive material are equal to each other in the image of the sample suitable for detecting an open defect and the state where a difference in brightness between the insulation material and the electrically conductive material is maximum in the image of the sample suitable for detecting a missing defect may be changed according to a material structure of the sample W and a pattern. Thus, if the structure of the sample W is changed greatly, the landing energy may be varied to check the material dependency of the brightness in the image of the sample W so that the sample surface observation is performed in an optimum state.

Figure 11:
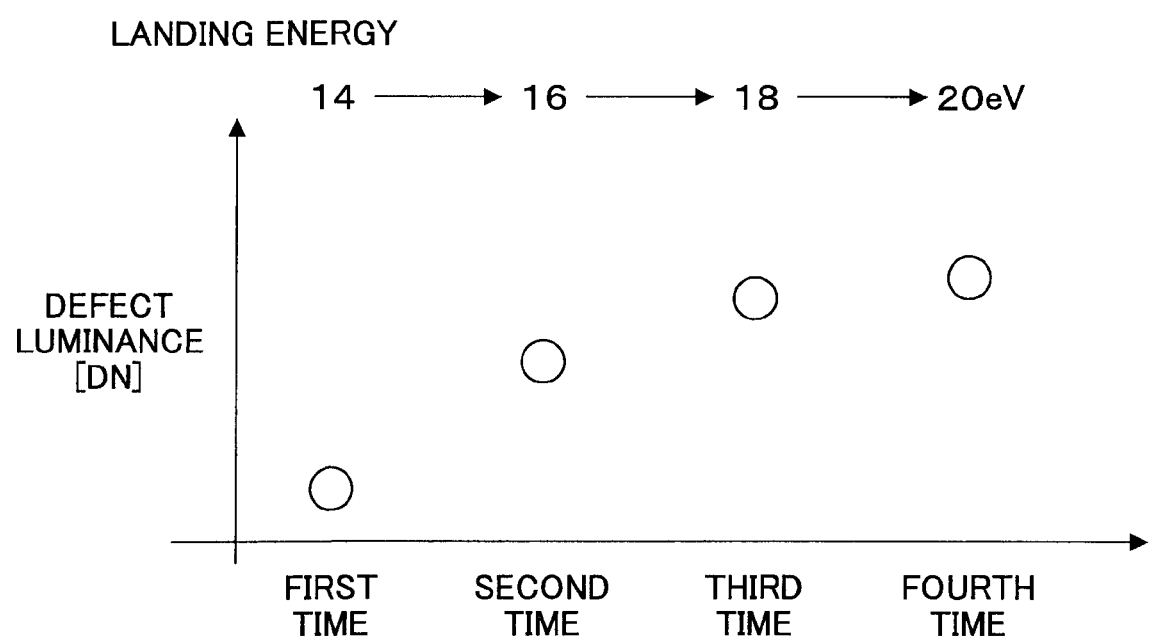
FIG. 11 is an illustration for explaining a variation of the sample surface observation method according to the embodiment of the present invention.

FIG. 11 is an illustration for explaining a mode of a variation of the sample surface observation method according to the present embodiment. In FIG. 11, the horizontal axis represents a number of times of irradiating the electron beam 15, and the vertical axis represents a brightness of a defect. In FIG. 11, changes in the brightness of a defect in an image of a surface of a sample according to the number of irradiation of the electron beams 15 and changes in the landing energy are indicated.

In the sample surface observation method according to the present embodiment, when the electron beam is irradiated onto the sample for a plurality of times and further the landing energy is gradually increased, the contrast (gradation level difference or brightness difference) of the defective position goes up. FIG. 11 indicates the state changes. That is, the electron beam 15 is irradiated for a plurality of times onto the surface of the sample while gradually increasing the landing energy to 14 (eV) at the first time of irradiation of the electron beam 15, to 16 (eV) at the second time of irradiation of the electron beam 15, to 18 (eV) at the third time of irradiation of the electron beam 15, and to 20 (eV) at the time of fourth irradiation of the electron beam 15. It can be appreciated from FIG. 11 that the brightness of the defect in the image of the sample goes up each time the number of irradiation is increased from the first time to the fourth time.

By using the above-mentioned phenomenon, in the variation of the sample surface observation method, after setting the state suitable for an open defect or a missing defect according to brightness as mentioned above, the electron beam may be irradiated for an appropriate number of times of irradiation and thereafter the defect detection may be performed. According to the variation of the sample surface observation method, a more accurate defect detection can be performed. On the other hand, if the number of times of irradiation is increased excessively, it takes a long time to observe a sample for one time, which may lower a throughput. Thus, it is preferable to set the number of times of irradiating the electron beam 15 with an appropriate balance. In the present variation, when the number of times of irradiation of the electron beam 15 is two to four times, an optimum defect detection can be performed from the view of the acquired image of the sample and from the view of the throughput.

In the present embodiment and variation, the method of observing the sample was explained by using the image projection type electron beam apparatus 100 using the electron beam 15 having a two-dimensional area, which electron beam 15 can be irradiated onto a camera which has several pixels. However, the present invention is not limited to this, and applicable to, for example, a scanning electron microscope (SEM) in which an electron beam is focused onto a single-pixel size. When using such an SEM-type electron beam apparatus, the energy of the electron beam is increased, and it is difficult to apply an electron beam of a low landing energy area as mentioned in the present embodiment and it is difficult to detect an open defect using the area 2. However, by using an area where the landing energy is 100 (eV) or more as shown in FIG. 4 and an area where a difference in brightness between the electrically conductive material and the insulating material is large, the detection of a missing defect can be performed easily and surely.

The present invention is not limited to the specifically disclosed embodiments, and variations and modifications may be made without departing from the scope of the present invention.

The present application is based on Japanese priority application No. 2007-259808 filed on Oct. 3, 2007, the entire contents of which are hereby incorporated herein by reference.

What is claimed is:

1. A sample surface observation method of observing a surface of a sample by acquiring an image of the surface of the sample, the sample surface observation method comprising:
   irradiating an electron beam onto the surface of the sample in which a pattern including an insulation material and an electrically conductive material is formed;
   detecting electrons that acquired structure information regarding a structure of the surface of the sample;
   acquiring an image of the surface of the sample by a result of the detection of electrons; and
   observing the surface of the sample using the acquired image of the surface of the sample,
   wherein the electron beam is irradiated onto the surface of the sample in a state where a brightness of the insulation material and a brightness of the electrically conductive material in the image of the surface of the sample are set equal to each other.

2. A sample surface observation method as claimed in claim 1, further comprising detecting, as an open defect in the surface of the sample, a brightness of a point different from a brightness of said insulation material and a brightness of said electrically conductive material in the image of the surface of the sample.

3. The sample surface observation method as claimed in claim 1, wherein a setting of a state based on the brightness of said insulation material and the brightness of said electrically conductive material in the image of the surface of the sample is performed by adjusting a landing energy when irradiating the electron beam onto the surface of the sample.

4. The sample surface observation method as claimed in claim 1, wherein the electron beam is a surface beam that irradiates a surface with two-dimensional area.

5. The sample surface observation method as claimed in claim 1, wherein the electron beam is irradiated onto the surface of the sample while gradually increasing a landing energy for a plurality of times.

6. A sample surface observation method of observing a surface of a sample by acquiring an image of the surface of the sample, the sample surface observation method comprising:
   irradiating an electron beam onto the surface of the sample in which a pattern including an insulation material and an electrically conductive material is formed;
   detecting electrons that acquired structure information regarding a structure of the surface of the sample;
   acquiring an image of the surface of the sample by a result of the detection of electrons; and
   observing the surface of the sample using the acquired image of the surface of the sample,
   wherein the electron beam is irradiated onto the surface of the sample in a state where a difference in brightness between said insulation material and said electrically conductive material in the image of the surface of the sample is maximum.

7. The sample surface observation method as claimed in claim 6, wherein the state where a difference in brightness between said insulation material and said electrically conductive material in the image of the surface of the sample is maximum is determined in a mirror electron area where electrons that has acquired the structure information of the surface of the sample turn into mirror electrons.

8. The sample surface observation method as claimed in claim 6, wherein a setting of a state based on the brightness of said insulation material and the brightness of said electrically conductive material in the image of the surface of the sample is performed by adjusting a landing energy when irradiating the electron beam onto the surface of the sample.

9. The sample surface observation method as claimed in claim 6, wherein the electron beam is a surface beam that irradiates a two-dimensional area.

10. The sample surface observation method as claimed in claim 6, wherein the electron beam is irradiated onto the surface of the sample while gradually increasing a landing energy for a plurality of times.

* * * * *